United States Patent [19]

Dow et al.

[11] Patent Number: 5,243,911
[45] Date of Patent: * Sep. 14, 1993

[54] ATTENUATOR FOR PROTECTING ELECTRONIC EQUIPMENT FROM UNDESIRED EXPOSURE TO RF ENERGY AND/OR LIGHTNING

[76] Inventors: Robert L. Dow, Rte. 5, Box 415, LaPlata, Md. 20646; Paul W. Proctor, Rte. 2, Kathy La., White Plains, Md. 20695

[*] Notice: The portion of the term of this patent subsequent to Aug. 6, 2008 has been disclaimed.

[21] Appl. No.: 794,126
[22] Filed: Nov. 12, 1991

Related U.S. Application Data

[63] Continuation-in-part of Ser. No. 584,045, Sep. 18, 1990.

[51] Int. Cl.[5] .......................... F42B 3/18; F42B 3/185
[52] U.S. Cl. ................................ 102/202.2; 102/202.3
[58] Field of Search ............... 102/202.1, 202.2, 202.3, 102/202.4

[56] References Cited

U.S. PATENT DOCUMENTS

| | | | |
|---|---|---|---|
| 2,821,139 | 1/1958 | Apstein et al. | 102/202.2 |
| 3,213,791 | 10/1965 | Schnettler | 102/202.4 |
| 3,264,989 | 8/1966 | Rucker | 102/202.2 |
| 3,572,247 | 3/1971 | Warshall | 102/202.2 |
| 4,103,619 | 8/1978 | Fletcher et al. | 102/202.5 |
| 4,306,499 | 12/1981 | Holmes | 102/202.4 |
| 4,378,738 | 4/1983 | Proctor et al. | 102/202.2 |
| 4,517,895 | 5/1985 | Rucker | 102/202.2 |
| 4,592,280 | 6/1986 | Shores | 102/202.2 |
| 4,848,233 | 7/1989 | Dow et al. | 102/202.2 |
| 5,036,768 | 8/1991 | Dow et al. | 102/202.2 |

*Primary Examiner*—Charles T. Jordan

[57] ABSTRACT

A device for preventing energy associated with nearby lightning strikes, electrostatic energy, and/or RF energy from damaging or inadvertently operating or actuating electronic equipment, such as an EED electrical initiation element, includes a bipartite faraday shield. One wall of the bipartite faraday shield is formed of a ferrite element such as disclosed in U.S. Pat. No. 5,036,768 and application Ser. No. 07/584,045. In some cases, the ferrite element can be doped with calcium oxide. The preferred doping range is between 1 and 20 ppm. A specific embodiment of the bipartite faraday shield includes an open-ended metal case with the ferrite device closing the open end of the case.

29 Claims, 4 Drawing Sheets

ATTENUATOR FOR PROTECTING ELECTRONIC EQUIPMENT FROM UNDESIRED EXPOSURE TO RF ENERGY AND/OR LIGHTNING

This application is a continuation-in-part of U.S. Ser. No. 07/584,045 filed on Sep. 18, 1990 (hereinafter referred to as the parent document), which was a continuation-in-part of U.S. Pat. No. 5,036,768 (hereinafter referred to as the grandparent). The disclosures of these two documents are incorporated herein by reference.

TECHNICAL FIELD OF THE INVENTION

The present invention relates to the general art of protecting electronic equipment and elements, and to the particular field of protecting electroexplosive devices. Specifically, the invention relates to protecting electroexplosive devices from inadvertent firing in a mining or tunneling operation.

BACKGROUND OF THE INVENTION

A faraday shield comprises a metallic cage or enclosure surrounding equipment or elements being protected from the effects of an electric field. An electric field set up outside the cage or enclosure has no effect on instruments or other electronic equipment located inside the cage or enclosure. A faraday shield generally requires some sort of pass-through element, such as a capacitor, in order for leads to extend into or out of the faraday shield to connect the electronic equipment inside the shield to equipment or systems located outside of the shield. It is imperative that no gaps exist between any screening and the leads associated with the shield. The pass-through elements can be used to prevent leakage paths into the enclosure while preventing shorting of the protected elements. However, the pass-through elements can be quite large and cumbersome thereby making the faraday shield large.

While effective for many applications, the size of the faraday shield may present a problem when the shield is applied to certain uses. This size drawback may even prevent use of a faraday shield in some situations. One such situation is in protecting electroexplosive devices (EEDs) from the effects of electric fields in the environment of the electroexplosive device (EED). Many uses of an EED require the EED to be smaller than presently available faraday shields will permit. One such use is in the mining and tunneling art. The uses of EEDs and the electromagnetic energy to which such EEDs might be exposed will be discussed below, with special emphasis being placed on the use of EEDs in the mining and tunneling industry.

An electroexplosive device is an initiator or a system in which an electrical impulse initiates detonation or deflagration of an explosive. An EED generally includes a power source electrically connected to an electrical initiation element (EIE) via input firing leads. The EIE is of the type which heats up when current is passed through it, and is in heat transferring contact with an explosive charge. When power is applied to the EIE, it heats up and eventually reaches a temperature which ignites the explosive charge contacting that EIE. Such EEDs are used in both the military market and in the civilian market for blasting applications, for ammunition applications as well as for air bags or the like. Because EEDs can rapidly generate large volumes of gas, they also can be used in conjunction with nearly any item which must be rapidly inflated.

As is well known to those skilled in the EED art, RF energy can cause an undesired actuation of an EED. RF energy incident on an EED can induce a current though the EIE of the EED. If the RF power level is high enough, or if the RF energy has a frequency which is high enough, the current induced in the EIE can become high enough to heat the EIE to a temperature which will activate the explosive charge thereby activating the EED in an undesired manner.

RF energy induced actuation of an EED is undesirable in any situation, and is especially undesirable if the EED is expected to be used in locations where there are high concentrations of high power RF and/or high frequency RF, such as near radar installations or the like. For this reason, many applications of EEDs, especially by the military, have extremely high standards for RF protection required for such EEDs.

As discussed in the incorporated documents, the EED art contains several devices which are intended to prevent undesired RF energy induced firing of an EED. Some of these devices include a Ferrite element surrounding the input leads. Some of these devices were discussed in the incorporated documents, and reference is made thereto for such discussion.

As discussed in these documents, the devices disclosed in the incorporated documents protect EEDs from inadvertent RF energy induced firing as well as from inadvertent electrostatic energy induced firing. These devices effect this protection by having an impedance path between the EED lead lines and ground which, for RF energy incident on the device, is lower than the impedance on the lead line to the firing element. Therefore, for a pin-to-case situation, current induced by RF energy induced potential is shunted to the case rather than flowing to the firing element via the lead line. Likewise, for a pin-to-pin situation, the current induced by RF energy-induced potential is simply dissipated as heat in the ferrite rather than flowing to the firing element. Therefore, the devices disclosed in the incorporated documents have shown outstanding protection features for EEDs that are exposed to high levels of RF and electrostatic energy. In fact, tests have shown that EEDs protected by the devices disclosed in the incorporated documents can be exposed to RF energy levels as high as fourteen watts at one megahertz and will prevent the EIE of the EED from being actuated by RF energy. Therefore, these devices have proved to be excellent protection against both RF and electrostatic energy.

As mentioned above, the mining and tunneling industry has long used EEDs. This industry has tried to protect the EEDs using several means, such as earthing devices, fuses, exploding bridgewires, frequency coded firing systems, or the like to protect the EEDs from inadvertent RF energy induced firing. While these devices have proved to be somewhat effective in limited situations, they still have several shortcomings that have generally limited their use.

In particular, the EEDs used in the mining and tunneling industry are subject to inadvertent detonation due to nearby lightning strikes, even lightning strikes occurring great distances from the EED, as well as due to inadvertent detonation due to RF energy generated by sources in the immediate vicinity of the mining or tunneling operation.

For example, some studies have concluded that surface lightning strikes occurring as much as twenty kilometers from the EED may generate currents that can endanger unprotected EEDs. As will be discussed in this disclosure, these stray currents can travel by several paths to reach the unprotected EED. Still further, other studies have concluded that high voltage power lines such as might be associated with an electrified trackway system, in the vicinity of a mining or a tunneling operation can generate sufficient RF energy to endanger unprotected EEDs used in the mining or tunneling operation.

In particular, in recent years, there has been a growing concern regarding safety-hazards due to nearby lightning effects in shallow coal mines. Several reported underground fatal accidents have been related to the passage of thunderstorms. Other more numerous incidents include electrical shocks, sparking from underground equipment, as well as premature and unexpected detonation of explosives in the charge faces and methane gas ignitions. These problems are of a serious nature, with a risk of serious injury or possibly death, to personnel in the vicinity of such an incident.

Presently, it is theorized that nearby lightning strikes and high voltage sources create adverse effects in a coal mine by several mechanisms:

(a) direct flow of lightning current through the rock formations surrounding a working coal face and in the face itself due to a strike close by; and/or (b) the transfer of a high potential by metalwork in the mine from a more or less remote point (e.g., an above-ground conveyor gantry) to the working face, following a direct lightning strike to the above-ground steelwork.

A voltage of about 50 kV has been measured between a coal face and earthed metalwork in a colliery, due to nearby lightning strikes. On various occasions, men have received electric shocks from roofbolts or machines during lightning storms. Such roofbolt paths may also endanger unprotected EEDs located nearby. Detonators (sometimes a number of detonators wired individually or connected in series) have been fired simultaneously by lightning currents.

These are clearly undesirable situations.

Figure 1:
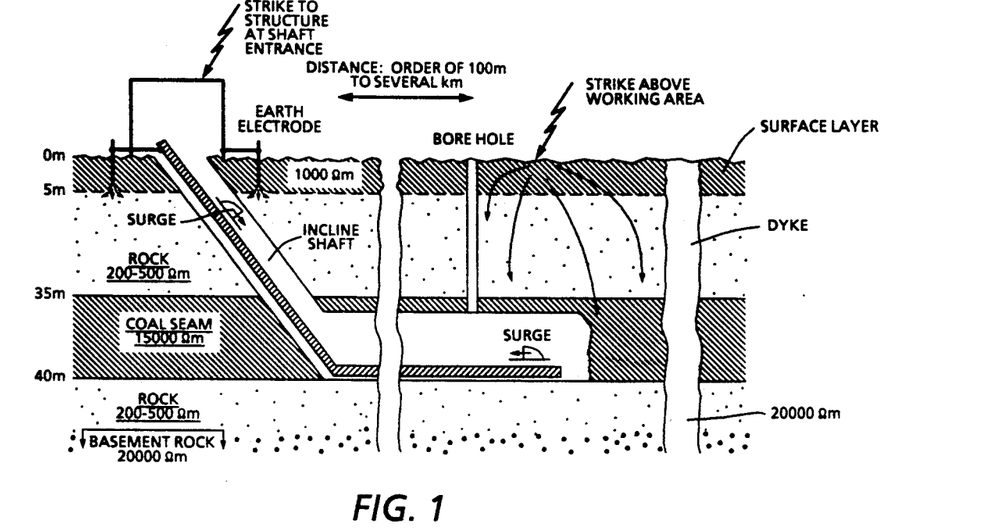
FIG. 1 illustrates a colliery situation in which above-ground lightning causes currents to flow into the mine or tunnel via various paths.

Several important features of a typical coal mine as well as possible lightning disturbance mechanisms are illustrated in FIG. 1.

As seen in FIG. 1, three basic mechanisms are thought to be responsible for the energy transfer from the surface to the coal face. These are electromagnetic induction, direct conduction and direct strike. The energy transfer may result ultimately in a voltage surge propagating through the mine via any conductive system that is available, such as the conveyor system, water pipes, housing of electrical equipment, armoring of cables, or the like to an unprotected EED. Therefore, any EED used in the mining or tunneling operation must be protected from inadvertent firing induced by any of these just-mentioned mechanisms.

The surge may be attenuated as it propagates through the mine due to losses in transmission path. However, since contact between the conductive system and the rock strata is usually poor, the wave can still propagate to the farthest extremities of most mines. The transmission line terminations near the mining face are most likely to be open circuit in nature and the surge would typically be reflected and doubled. This would lead to an increased concentration of potentials thereby increasing the danger to unprotected EEDs.

The ways in which the travelling wave is initiated vary for the different mechanisms, and all may endanger EEDs or other electronic equipment used in a mining or tunneling operation. In the simplest case, i.e., a direct strike to a structure at a shaft entrance or ventilation shaft, a voltage surge is the only energy transfer mechanism involved. The local injection of lightning current into the earth via an electrode system causes the potential of the structure to rise in relation to a remote earth.

A more complex situation arises when there is a lightning strike on the surface away from the shaft. Here, electromagnetic induction and/or direct conduction are the relevant energy transfer mechanisms.

For the latter situation, the conductive path through the intervening rock and soil media is augmented underground by any of the conductive systems mentioned above. A voltage surge results from the steep potential gradients formed when the current distribution is distorted. Local variations in the terrain, such as dikes, boreholes, and geological faults, the mine excavations and the underground conductive systems can all locally distort the current and thus initiate a surge. A cased borehole would provide an excellent conductive path form the surface into the mine.

The third mechanism, i.e., electromagnetic induction, is possible since the electromagnetic fields associated with the discharge of the lightning channel are very high. These fields penetrate through the overlying ground into the mine tunnels. A current, and therefore a voltage surge, is induced into any conductive system situated in the electromagnetic field. In this case, energy may be transferred to the coal face not only via the propagating voltage surge but also through the electromagnetic fields themselves. In fact, a wave guide effect may be present since the coal seam, of high resistivity, is surrounded by shale of low resistivity. For the same reason, a capacitive effect may also be present.

As mentioned above, the voltage surges propagate along any conductive path, including the armorings of cables and housing of electrical apparatus. These are often operated in close proximity to the charged faces In the case of the voltage surge, the conductive system will act as a radiating source, with the electromagnetic wave being radiated from its termination point. Where the electromagnetic fields are the only means of energy transfer, the lightning strike is the source. The amount of energy available for coupling into the detonator and exploder circuits depends on several factors. The rates of decay of the electric and magnetic field components with distance from the source are relevant. Thus, the position of the source is important. The field strength at any point also depends on the strength of the source (e.g., voltage surge magnitude) and the characteristics of the radiating and receiving antenna associated with the unprotected EED. The fact that the conductive system terminations are open circuit in nature is, therefore, very significant. The radiation, induction and quasi-static field components could all be important depending on the distance between source and receiver.

For all cases, the detonator and exploder circuits will act as "receiving antennas." The amount of energy extracted from the electromagnetic field will depend on various factors, including the conductor geometry, length and orientation relative to the incident field vector. In the case of a loop formed by the detonator wires, the area enclosed by the loop is also important. The energy will be maximum when the "receiving antenna" is made up of single wires, but will be greatly reduced by mutual coupling if the wires are twisted pairs construction. Accordingly, any EED design must account for this "antenna" effect as well, and not have the design protect against one form of energy transfer to the EED, while increasing the undesirable portions of the "antenna" effect.

A premature detonation will occur if the energy, i.e., current flowing into the circuit, is large enough to heat the detonator EIE. Any of these above-mentioned situations and conditions may create a situation in which an unprotected EED or other electronic equipment is subjected to sufficient energy to damage or inadvertently operate it.

The industry has therefore used several methods of combating risks underground due to currents caused by lightning. For example, all metalwork at shaft collars are usually earthed, parallel and adjacent metalwork are generally bonded underground, underground metalwork is usually maintained as close to the potential of the surrounding ground as possible by electrical bonding of that metalwork in groups to existing roofbolts installed to maintain a safe roof in the mine.

To combat lightning and certain induction or other stray current situations in collieries, it may even be necessary to establish earthing electrodes underground with sufficiently low impedance to earth.

While such devices and methods as discussed above have been somewhat effective, these devices and methods still have not been entirely effective in all situations and are not fully effective against protecting EEDs against RF-energy induced firing while maintaining an antenna profile that is as small as possible.

A faraday shield would vitiate, if not totally eliminate, this antenna effect while establishing effective protection for an EED. However, EEDs used in the mining and tunneling industry have size limitations. As mentioned above, the requirements for a pass-through capacitor element on a faraday shield prevents use of such devices to protect an EED in many mining and tunneling operations.

Therefore, there is a need for a means to protect electronic equipment such as EEDs, used in mining or tunneling operations from inadvertent damage or detonation caused by nearby lightning strikes or from RF energy. Specifically, there is a need for a faraday shield that is amenable to use in mining and tunneling operations.

OBJECTS OF THE INVENTION

It is a main object of the present invention to provide a device for protecting an electronic element from adverse effects of RF energy and/or nearby lightning strikes.

It is another object of the present invention to provide a faraday shield that can be used to protect an electronic element from adverse effects of RF energy and/or lightning.

It is another object of the present invention to provide a device for protecting an EED in a mining or tunneling operation.

It is another object of the present invention to provide a device for protecting an EED in a mining or tunneling operation from inadvertent firing caused by RF energy incident on the EED.

It is another object of the present invention to provide a device for protecting an EED in a mining or tunneling operation from inadvertent firing caused by RF energy incident on the EED while also protecting the EED from lightning-induced energy from inadvertently firing the EED.

It is another object of the present invention to provide a faraday shield for protecting an EED in a mining or tunneling operation from inadvertent firing caused by RF energy incident on the EED while also protecting the EED from lightning-induced energy from inadvertently firing the EED.

It is another object of the present invention to provide a device for protecting an EED in a mining or tunneling operation from inadvertent firing caused by RF energy or lightning induced energy incident on the EED while maintaining a low antenna profile.

It is another object of the present invention to provide a faraday shield for protecting an EED in a mining or tunneling operation.

It is another object of the present invention to provide a Faraday shield for protecting an EED in a mining or tunneling operation from inadvertent firing caused by RF energy incident on the EED.

It is another object of the present invention to provide a Faraday shield for protecting an EED in a mining or tunneling operation from inadvertent firing caused by RF-induced energy or lightning-induced energy incident on or transferred to the EED.

It is another object of the present invention to provide a device for protecting an EED in shallow mines and underground excavations from inadvertent ignition or actuation caused by nearby above-ground lightning strikes occurring at distances a far away as twenty kilometers.

It is another object of the present invention to provide a device for protecting an EED in a mining or tunneling operation in both a pin-to-pin and pin-to-case situation.

It is another object of the present invention to provide protection to an EED from inadvertent actuation caused by above-ground lightning strikes and to provide protection in both pin-to-pin and pin-to-case ignition and actuation routes.

It is another object of the present invention to provide a complete faraday shield over the entire surface of an EED in a practical manner.

It is another object of the present invention to provide a complete faraday shield for an EED that also provides protection from stray RF energy both in pin-to-pin and pin-to-case modes, while also providing broadband RF protection from a single impedance or ferrite device.

It is another object of the present invention to provide a complete faraday shield for an EED that also provides protection from stray RF energy both pin-to-pin and pin-to-case modes, provides broadband RF protection from a single ferrite device while also providing electrostatic protection in pin-to-pin and pin-to-case modes and does not change the all-fire or no-fire EED requirements placed thereon.

It is another object of the present invention to provide a device for protecting an EED in a mining or tunneling operation that can be used in conjunction with a firing line filter.

It is another object of the present invention to keep the broadband RF and electrostatic protection of EEDs provided in the device disclosed in the incorporated documents while still providing protection against inadvertent firing of such EEDs due to above-ground lightning.

It is another object of the present invention to provide a faraday shield that uses an intermediate conductivity ferrite element as one component of the faraday shield.

It is another object of the present invention to provide a faraday shield that minimizes the antenna effect for receiving electromagnetic pulses transmitted by above-ground lightning and by RF transmitters used in the vicinity of a mining or tunneling operation.

It is another object of the present invention to provide a single ferrite device that performs multiple functions associated with protecting an EED against RF, electrostatic, and above-ground lightning-induced inadvertent initiation and actuation.

SUMMARY OF THE INVENTION

These, and other, objects are achieved by using the protection devices disclosed in the incorporated documents as one wall or part of a faraday shield. Such a bipartite faraday shield has particular application to protecting EEDs used in mining or tunneling operations. The ferrite element is doped with calcium oxide. The doping is specifically within the range of 1 ppm to 20 ppm. The specific amount of calcium oxide is selected to adjust the internal DC resistance of the ferrite element to be higher than the DC resistance of the EIE located within the faraday shield to prevent shorting of that element, yet is near the DC resistance of the remainder of the faraday shield wall to preserve the integrity of the faraday shield. The doped ferrite element is then force fit into the metal wall to provide an integral bipartite faraday shield.

The doped Ferrite element of the disclosed protection devices has a slightly lowered RF attenuation capability; however, the RF attenuation capability of the disclosed Ferrite devices is so high, that a slight lowering thereof is nearly inconsequential. The doped Ferrite element used in the device of the present invention has the following characteristics:

it is large enough in size to withstand the full impact of nearby lightning-induced energy incident thereon at an underground location in a mine or tunnel without disintegrating;

the dielectric coefficient thereof is high enough to allow capacitor charging during the rise time and duration of a lightning pulse without causing capacitor failure;

the controlled DC resistance thereof is high enough to allow slow dissipation of the stored energy in a controlled manner to prevent inadvertent firing during discharge;

all of the leads associated with the device embodying the present invention and the conductive case are tied together in a controlled resistive network so that electrostatic potentials high enough to cause inadvertent firing do not occur; and an electric blasting cap can survive nearby lightning strike and will still respond to the correct DC firing pulse.

In this manner, an EED or other electronic element protected by the device of the present invention will be able to withstand repeated nearby lightning strikes without appreciably changing the physical properties and without inadvertent firing, while also being able to repeatably withstand high levels of RF energy, and yet will still fire when desired.

The bipartite faraday shield using the doped ferrite element acts as a true faraday shield, yet does not require pass-through capacitor elements as the doped ferrite element replaces the function, operation and results associated with such pass-through capacitor elements. The preferred form of the bipartite faraday shield includes a metal open-ended case in which one of the ferrite devices disclosed in the incorporated patents but doped with calcium oxide is used to electrically close the open end. Electronic equipment being protected is located inside the metal case, and thus the metal case, closed by the modified ferrite device, acts as a completely encompassing faraday shield. For the purposes of this disclosure, since the shield includes a metal case as well as a ferrite closure plug, the overall shield will be referred to as a bipartite faraday shield.

The bipartite faraday shield embodying the present invention is small enough to be used in mining and tunneling operations. The bipartite faraday shield also greatly reduces, or even eliminates, the antenna effect discussed above.

Still further, by using the ferrite element disclosed in the incorporated documents, the bipartite faraday shield retains all of the advantages associated with that ferrite element as discussed in the incorporated documents. Thus, the pin-to-pin and pin-to-case protection for RF energy of the ferrite element is retained, as well as the protection against electrostatic energy. In essence, all of the advantages associated with the ferrite element disclosed in the incorporated documents are added to the advantages associated with a faraday shield, while eliminating the disadvantages associated with the pass-through capacitor elements normally required for a faraday shield—all without degrading the performance associated with a faraday shield. In fact, since the pass-through capacitor elements are eliminated in the bipartite faraday shield embodying the present invention and replaced by the ferrite element disclosed in the incorporated documents, the overall performance characteristics of a faraday shield may be enhanced for some situations.

Due to the factors discussed above, a practical, low cost, and effective faraday shield has never been used in conjunction with an EED in general, and in conjunction with an EED used in a mining or tunneling operation in particular. However, the bipartite faraday shield of the present invention is entirely amenable to such use.

The doped ferrite attenuator forms a portion of the electrically conductive enclosure thereby maintaining the advantages of a faraday shield while also attenuating RF energy incident thereon as discussed in the incorporated documents. The dual protection is extremely valuable in many situations, but is especially valuable in a mining or tunneling operation that may subject EEDs to the adverse effects of nearby lightning strikes and/or RF energy from adjacent sources.

DETAILED DESCRIPTION OF THE PREFERRED EMBODIMENT OF THE INVENTION

Figure 2:
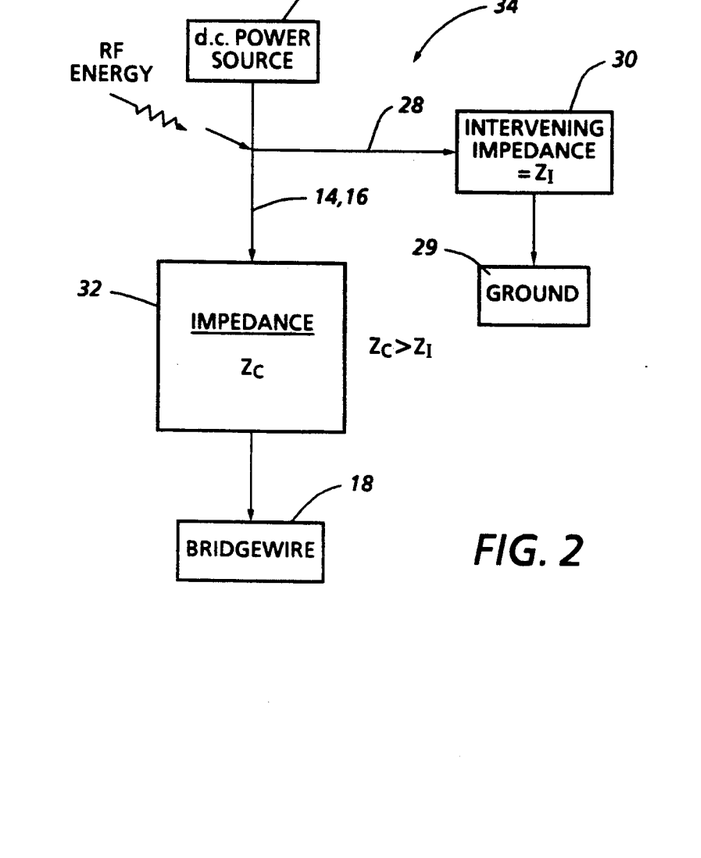
FIG. 2 is a block diagram representing the invention disclosed in the parent application in which the electrical path through an input lead to a bridgewire in an EED has an impedance that is higher than the impedance on an alternate route to ground when the device is exposed to RF energy.
Figure 3:
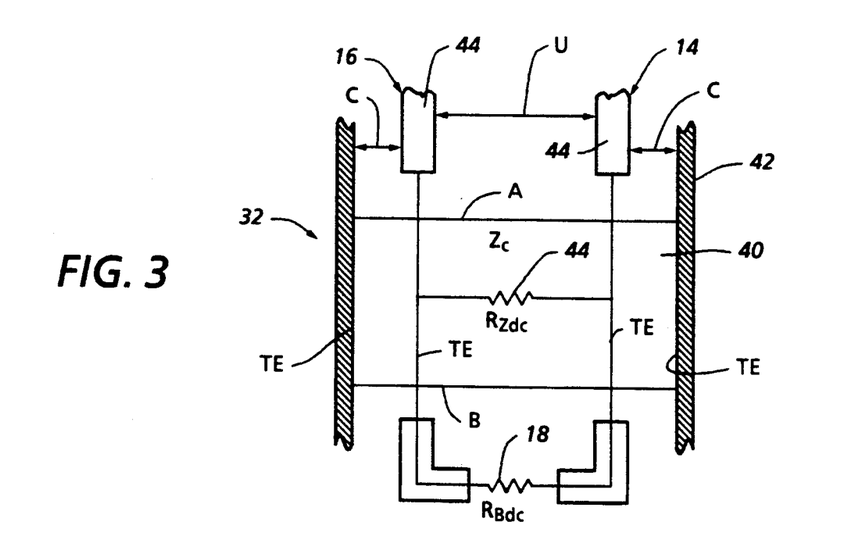
FIG. 3 is a block diagram representing one embodiment of the invention disclosed in the parent application in which the EED includes a ferrite element electrically and thermally connected both to the input leads of the EED and to the electrically and thermally conductive case of the EED.

Referring to FIGS. 2 and 3, which correspond to FIGS. 4 and 5 in the parent document, the invention disclosed therein is embodied in a means for increasing the value of the impedance on input leads 14 and 16 between the dc power source 12 and the bridgewire or EIE 18 to a value greater than that impedance $Z_I$ associated with the path 28 from the input leads to each other or from the input leads to the ground element 29. In this manner, the energy associated with the RF energy incident on EED 34 will either be simply blocked by the impedance on the input leads, or will move to ground via the lower impedance path 28 to ground or will simply be dissipated in the impedance element 32 instead of moving through the input leads to the EIE.

This is illustrated in FIG. 2 by impedance element 32 located in the input leads 14 and 16 between the dc power source 12 and the EIE 18 of EED 34. The impedance element 32 has an impedance $Z_C$ which is greater than the impedance value $Z_I$ whereby the energy associated with RF energy incident on the EED 34 will "see" a path of lower impedance to ground 29 than to the EIE 18. This energy will therefore tend to flow to ground instead of to the EIE. This energy will either jump to ground in a pin-to-case situation, or simply be dissipated as heat in the element 32 in a pin-to-pin situation.

Once the RF energy or frequency exceeds certain critical values, the EED 34 forces the energy to ground instead of permitting it to pass to the EIE. The EED 34 forces this energy to flow to ground 29 over the alternative path 28 instead of to the EIE because the impedance $Z_C$ of the element 32 in EED 34 is higher than the impedance $Z_I$ of the path 28. This is in contradistinction to the situation in EEDs known prior to the inventors' disclosure in which the impedance $Z_I$ of path 28 exceeds the impedance $Z_C$ of EED.

Since the value of $Z_I$ is determined according to the material properties of the path 28, this value can be obtained from various handbooks, such as the "Handbook of Modern Electronics and Electrical Engineering" edited by Charles Belove and published in 1986 by Wiley Interscience, see e.g., Chapters 8 and 9 of this handbook, the disclosure of which is incorporated herein by reference. The value of $Z_C$ is also determined according to the properties of the materials, and can be determined by using the same standard handbooks, as well as special textbooks, such as "Ferrites" by J. Smit and H. P. J. Wijn and published in 1959 by John Wiley & Sons. See e.g., pages 229 to 297, the disclosure of which is incorporated herein by reference. Other handbooks, such as Mechanical Engineers' Handbooks or Electrical Engineers' Handbooks, Physics Handbooks and the like all contain information necessary to determine the values of $Z_I$ and $Z_C$.

A preferred form of the impedance element 32 is shown in FIG. 3 as including a Ferrite element 40 electrically connected to the input leads 14 and 16 and electrically connected to electrically conductive case 42 of the EED. The electrical connection between the input leads and the Ferrite element is effected by skinning insulation 44 from the leads 14 and 16 and establishing direct electrical connection between the leads and the Ferrite element inside that element as shown in FIG. 3. However other electrically conductive paths through the Ferrite element can be used. The only requirement is that the input lead electrical path make electrical contact with the Ferrite element. Preferably, this electrical contact between the input lead and the Ferrite element occurs over substantially the entire length of the Ferrite element as measured along the input leads between locations A and B shown in FIG. 3. By being electrically connected to the Ferrite element over substantially its entire length, any variations in physical properties of the Ferrite element are "averaged out" so the overall properties of the impedance element are predictable. Likewise, the Ferrite element 40 is electrically connected to the case 42 over substantially the entire length of the Ferrite element as measured along the case between points A and B. This electrical connection between the Ferrite element and the conductive case over substantially the entire length of the Ferrite element also "averages out" any variations in Ferrite properties as may occur. Such electrical connection increases the impedance existing in the input leads between the dc power source and the EIE 18 by adding the impedance of the Ferrite element 40 and the impedance associated with the case 42 to the wires in a direct electrical connection rather than via an indirect manner which would occur if the Ferrite element were electrically insulated from the input leads and from the case 42 as is the situation in EEDs known prior to applicants' disclosure. Therefore, the value of $Z_C$ corresponds to the total impedance of the firing input leads plus the impedance associated with the conductive case plus the impedance associated with the Ferrite element 40; whereas the value of $Z_I$ corresponds to the impedance of the path between the firing input leads (pin-to-pin) at location U, or to the impedance between either input lead and the conductive case at locations C (pin-to-case).

However, while increasing the impedance on the input leads of the EED 34, the direct electrical connection between the electrically conductive Ferrite element 40 and both of the input leads 14 and 16 creates an electrical path between the lead 14 and the lead 16 and between both of these leads and the electrically conductive case 42. This path can short the leads and prevent a dc current from the dc power source from activating the EIE in a case where firing of the EED is intended.

To prevent this shorting of the leads 14 and 16, the Ferrite element 40 is selected to have an internal DC resistance 44 that is in excess of the resistance associated with the EIE. As indicated in FIG. 3, the internal DC resistance $R_{Zdc}$ associated with the Ferrite element which tends to define a DC electrical path between the input leads 14 and 16, is greater than the DC electrical resistance $R_{Bdc}$ associated with the EIE 18. In this manner, the DC path between the input leads and between the input leads and the conductive case has a DC resistance great enough so that the DC firing current will reproducably flow to the EIE rather than be shorted from one input lead to the other or from one input lead to the case.

While various forms of Ferrite can be used, one form of the Ferrite element 40 is sold by Ceramic Magnetics Corp. of Fairfield, N.J. under the name MN-67. Another effective material for the Ferrite element 40 is sold by the same company and has an elemental analysis that corresponds to a macro analysis of $MnO_{0.45}Zn_{0.3}FeO_{0.25}Fe_2O_4$. This particular formulation provides a significant RF attenuation below one megahertz and is even effective above the 20 gigahertz region. In fact, this formulation provides significant RF attenuation even in the 10 kilohertz region. Furthermore, the Curie Temperature of this material is in excess of 180° C. and preferably is in the range of about 250° C. to about 280° C. This high Curie Temperature has not been available before in combination with the other desirable physical properties stated above. Heretofore, the maximum heating that the inventors have been able to obtain using prior EEDs is about 150° C. The Ferrite element formed of this material can be processed to give strong Ferrite devices that withstand assembly operations without excessive breakage.

This formulation can be produced into several different Ferrite devices, including one hole beads, two hole baluns, or multiple hole chokes. It has been observed that the RF power attenuated by these devices increases in the order listed. For purposes of this disclosure, a bead has one hole, and is placed on a lead in the manner of a strung bead; a balun has two holes and can accommodate two wires or conductors; and a choke has multiple holes. One or more wire firing leads can also be used.

RF powers in excess of 100 watts may be safely attenuated using the system of the present invention. RF powers as high as 40 watts and RF frequencies as high as 20 gigahertz have been safely attenuated using the system shown in FIG. 3 without firing the EIE. The high powered energies are attenuated by the system of the present invention by establishing an arc from the input leads to the conductive case or between the input leads. This arcing has been found to be quite reliable and repeatable. The EEDs protected using the impedance element shown in FIG. 3 have also withstood exposure to radar, exposure to continuous transmission of RF power and to pulsed or intermittent transmission of RF power.

Other magnetic conductors can be selected by matching the requirements of the specific application to material characteristics such as frequency of operation, energy losses, stability, physical requirements, cost, manufacturability, availability and the like. Conductors can also be selected according to values of saturation induction, permeability, resistivity, and the like. Standard handbooks and textbooks such as the above-mentioned handbooks and textbooks present tables, formulae and criteria which can be used to select the ideal material and determine the values of impedance for the particular application whereby the elements of the EED 34 can be selected to satisfy the criterion set forth above that, for the expected range of RF power and RF frequencies, the impedance of the electrical path on the input leads between the dc power source and the bridgewire is greater than the impedance between the input leads and ground.

Variation of the Manganese-Zinc Ferrite formulation by increasing the overall iron content of the element can also be used to change the characteristics of the Ferrite element 40. For example, the Ferrite element can be an iron rich, manganese-zinc ferrite of special formulation.

It has also been found that the direct electrical contact between the Ferrite element 40 and the case and the input leads tends to dissipate static electricity by providing a direct electrostatic path to ground. Due to this direct electrostatic path to ground, the EED 34 can withstand electrostatic potentials which are extremely high as compared to those electrostatic potentials which will cause the EIE of EEDs known prior to applicants' disclosure to fire while not requiring any additional elements to dissipate static discharge. It has also been found that the element 40 can withstand repeated exposure to the high electrostatic potential without changing the properties of the ferrite.

By way of example, EEDs using either a Ferrite element made of the special formulation disclosed above or MN-67 Ferrite and set up to have the Ferrite element electrically connected to the input leads and to the conductive case as shown in FIG. 3 and as discussed above, have withstood an electrostatic potential of 60,000 volts without causing inadvertent actuation of the EIE to fire the device. This is compared to electrostatic potentials of approximately 30,000 volts which will fire EEDs known prior to applicants' disclosure. Due to this ability to dissipate extremely high electrostatic potentials, the EED of the present invention does not require any additional elements for dissipating electrostatic potential.

For Ferrite devices to have MIL STD 1385B broad bandwidth attenuation, most of the devices such as EEDs known prior to applicants' disclosure require external capacitors to be effective. Ferrite beads have only small capacitive effects, and Ferrite baluns can be made so the two holes thereof are parallel to provide increased capacitive effect as compared to a bead. However, these capacitive effects may be difficult and expensive to provide. The EED of the parent and grandparent disclosures do not require any external capacitor to meet MIL STD 1385B broad bandwidth requirements.

A still further preferred form of the invention includes the Ferrite element 40 in direct thermal contact with the input leads and in direct thermal contact with the case 42. This is indicated in FIG. 3 by indicators TE to denote that both electrical and thermal contact is made between the input firing leads and the impedance element and between the impedance element and the case which is both electrically and thermally conductive. The case 42 is usually a rather large (as compared to the Ferrite element) mass. The large mass of the case and large surface to transfer the heat energy is less susceptible to rapid thermal changes due to transient conditions than smaller masses, and tends to stabilize in temperature for the purposes of maintaining stable and predictable physical properties of the overall element 32, such as RF attenuation properties as well as physical size. Therefore, the direct thermal contact between the Ferrite element and the case 42 permits the overall impedance element 32 to maintain stable, and repeatable characteristics even when the device is exposed to rapidly changing conditions, or to conditions that are different than those conditions for which the device was designed.

The thermal contact between the Ferrite element and the case also protects against the probability of cooking off temperaturesensitive explosive components in the EED because a portion of the energy that otherwise would have gone into heating the Ferrite element is transferred to the case, and from the case to the environment thereby lowering the maximum internal temperature that the EED will experience. This thermal contact will also provide protection against the Ferrite element reaching its Curie Temperature.

Figure 4:
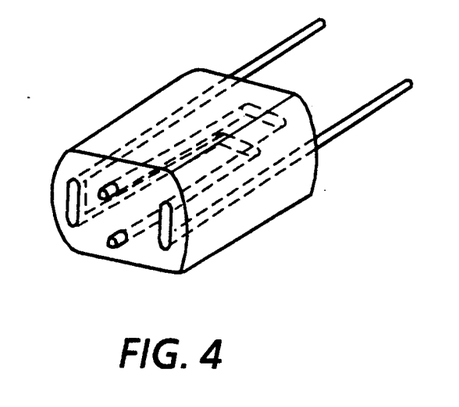
FIG. 4 is a perspective view of a bottom portion of a device disclosed in the grandparent document and illustrates one form of the device.
Figure 5:
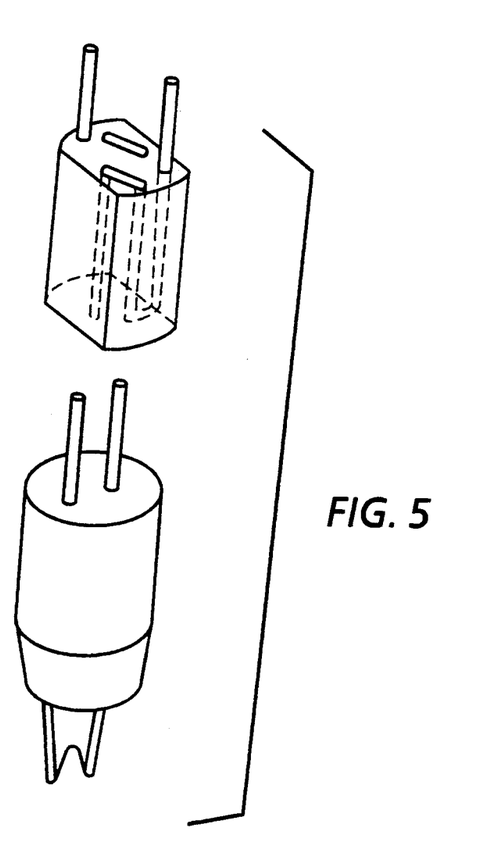
FIG. 5 is a perspective view of another form of the device disclosed in the grandparent document.
Figure 6:
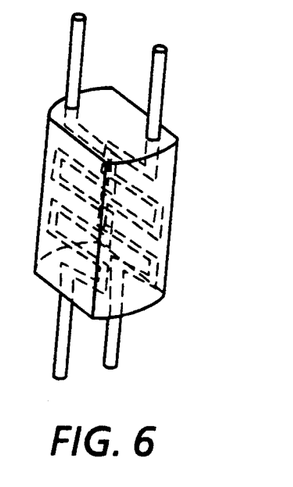
FIG. 6 is a cross-sectional view of an EED utilizing a single wire attenuator as disclosed in the grandparent document.

Various alternative forms of the impedance element 32 are possible within the scope of the present invention. For example, instead of using a Ferrite element, the input leads can be wound within the case or about a core in a manner to provide an inductor having an impedance within the above-stated criteria. In alternative forms of the Ferrite-less impedance element, the input leads can be formed of either non-magnetic, but electrically conductive, conductors, or of magnetic conductors preferably with a high magnetic permeability iron-cobalt alloys depending on the coil design. The input lead or leads can also be formed of paramagnetic material if suitable. Other winding patterns are discussed in the parent application to which reference is made. However, for the sake of completeness, two different winding patterns within a Ferrite element are disclosed in FIGS. 4, 5 and 6 herein, with these winding patterns within a Ferrite element being fully disclosed in the parent application. Other winding patterns are also possible including the spiral winding pattern disclosed in U.S. Pat. No. 4,848,233, the disclosure of which is incorporated herein by reference.

Figure 7:
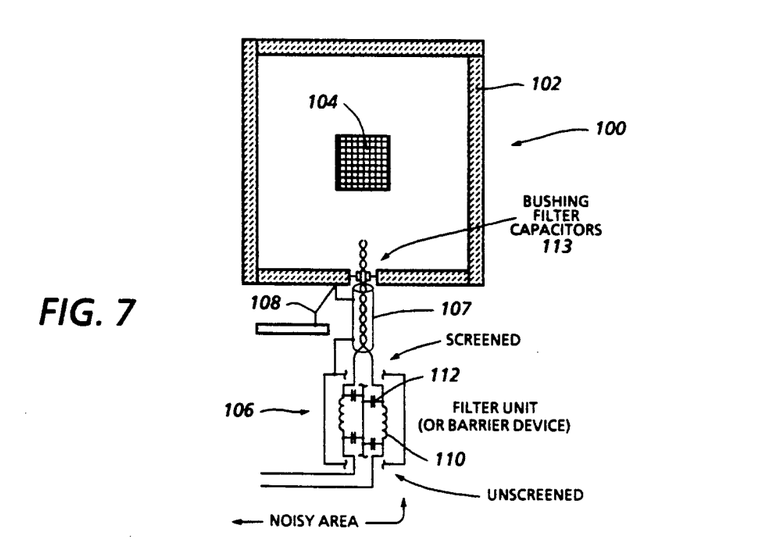
FIG. 7 illustrates a faraday shield in combination with a capacitive wound filter unit.

A faraday shield 100 is illustrated in FIG. 7, and includes a metallic wall 102 surrounding a device to be protected, such as an EED EIE 104. This faraday shield is connected to a filter unit 106 and a lead 107, and is earthed at location 108. The filter unit can include various resistance elements, as well as various inductive elements, such as inductor 110 and capacitive elements, such as capacitor 112. Other elements, such as MOVs (metal oxide varistor), or the like can also be used in the filter element. As is shown in FIG. 7, the faraday shield includes a pass-through capacitor element 113. Pass-through elements have been found to be necessary to prevent degradation of the faraday shield. However, elements associated with passing leads through wall 102 in prior faraday shields generally make the overall device too large for practical use in a mining or tunneling operation.

The present invention is embodied in a device that has a ferrite element as discussed above used as one part or wall of a faraday shield. The device can be doped or used directly as disclosed in the parent and grandparent documents, with the doping being used to adjust the internal DC resistance of the ferrite element whereby the protected element will not be shorted yet the faraday shield will not be degraded. It has been found that doping ranges between 1 ppm to 20 ppm of calcium oxide in the ferrite element are most effective. The preferred doping is about 10 ppm in any ferrite formulation including the $MnO_{0.45}Zn_{0.3}FeO_{0.25}Fe_2O_4$ formulation disclosed above. For example, as discussed in the incorporated documents, an internal DC resistance of between 3,000 Ω and 50,000 Ω is used, with an internal DC resistance of 3,800 Ω being preferred. The exact value of the internal DC resistance is set by doping the ferrite element with an appropriate amount of Calcium Oxide. The internal DC resistance of the ferrite element can be determined using the techniques disclosed in co-pending patent application Ser. No. 07/672,450, filed on Mar. 20, 1991, the disclosure of which is incorporated herein by reference.

The bipartite faraday shield is to be used to protect an electronic device from the effects of nearby lightning. The bipartite faraday shield of the present invention retains all of the desirable characteristics of a faraday shield; however, the ferrite element of the incorporated documents is used in place of one wall or one part of the faraday shield so the large passthrough elements can be eliminated. The ferrite element completes the faraday shield, yet permits wires or leads to pass into or out of the faraday shield without requiring use of the passthrough elements. Still further, the ferrite element adds all of the protection and advantages discussed in the incorporated documents to the protection of a faraday shield.

Figure 8:
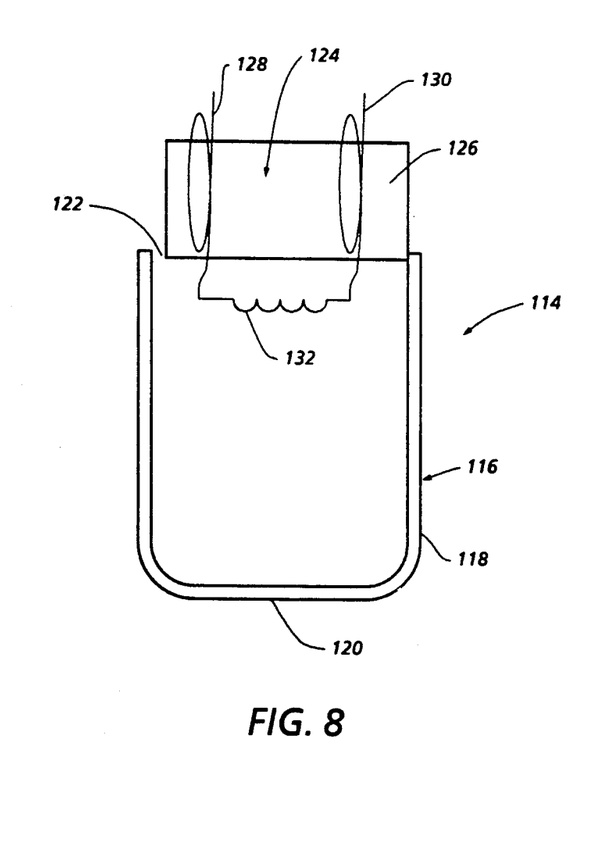
FIG. 8 illustrates an exploded elevational view of a bipartite faraday shield of the present invention in which one portion of the shield is formed by an attenuator disclosed in the parent and grandparent documents and the other part is formed by a metal case with the EIE of an EED being located inside this bipartite faraday shield.

A bipartite faraday shield embodying the present invention is illustrated in FIG. 8 by reference number 114. The bipartite faraday shield 114 includes a metal case 116 that includes a wall 118 on a base 120. The wall and base define an open-ended container with end 122 being open. A device 124 that is similar to the protection elements discussed above with regard to FIGS. 2 and 3 is inserted into the open-ended container via the open end 122. The device 124 includes a ferrite element 126 through which firing leads 128 and 130 extend. The firing leads are in electrical and thermal contact with the ferrite element as discussed above, and the ferrite element is inserted into the container to make electrical and thermal contact with the wall 118 of that container. The leads can be single or multiple pass as desired. An EIE 132 is connected to the leads as discussed above. As just discussed, the element 124 can be doped with carefully controlled amounts of calcium oxide, with the bipartite faraday shield protecting the EIE from inadvertent firing or actuation due to exposure to currents associated with nearby lightning strikes. However, the device 124 also protects the EIE against inadvertent firing or actuation due to RF or electrostatic energy incident on the overall device in the manner discussed above and in the incorporated documents. A filter unit, similar to the filter unit 106, can also be used in combination with the bipartite faraday shield 114. Use of the element 124 eliminates the need for pass-through elements.

Figure 9:
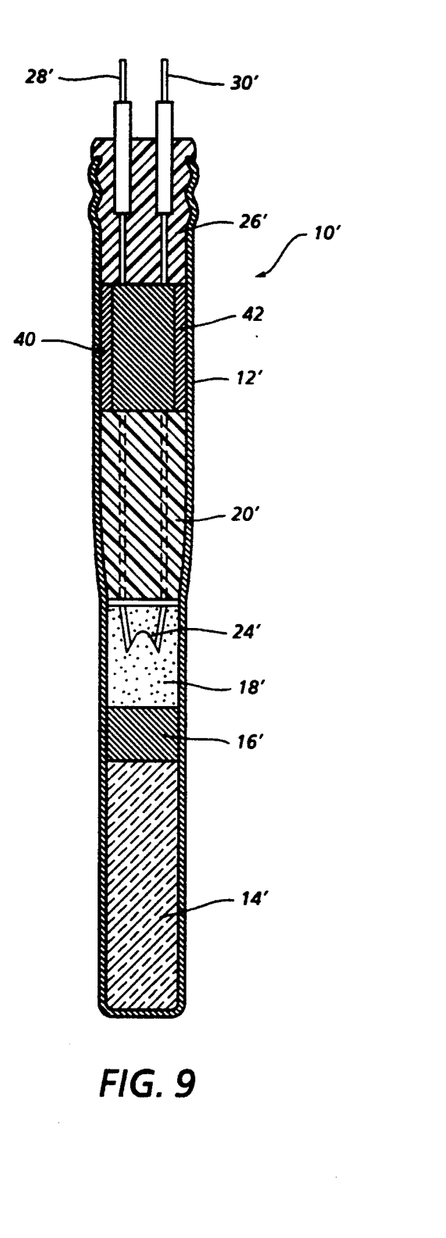
FIG. 9 is a cutaway elevational view of an EED embodying a protective device to be protected against inadvertent operation caused by the effects of nearby lightning strikes.

The device 10' shown in FIG. 9 is a form of the bipartite faraday shield in that the metal case 42 corresponds to the metal case 116, and the device 40 corresponds to the device 124, and EIE 24' corresponds to EIE 132.

The devices 114 and 10' are used in the manner discussed in the incorporated documents, and are used in the manner of any other EED. Therefore, no discussion regarding the use and operation of the EED incorporating the bipartite faraday shield will be presented.

By using a complete faraday shield around the EED, electromagnetic energy in the form of pulse (nearby lightning) or continuous (in the form of transmitted RF signals) cannot penetrate to the inside of the EED. Furthermore, the bipartite faraday shield greatly reduces the size or eliminates the antenna presented by the EED.

The selected ferrite provides an attenuating mechanism for dissipating the induced electromagnetic pulse generated by nearby lightning striking the surface of the ground above a mine or a tunnel. Because of the very fast rise time of the lightning pulse of about 4 μsec, the ferrite does not need to be an effective RF attenuator below 20 kHz. The ferrites of the present disclosure and of the incorporated disclosures have this capability.

The EED disclosed herein has sufficient contact areas between the ferrite element and the conductive case and between the ferrite element and the firing leads to safely, repeatedly, and without measurable change to the ferrite device, safely pass the energy surges associated with the induced energies trying to pass into the EED to initiate or actuate the EED and dissipate them harmlessly to ground or internally in the ferrite device. The ferrite device can safely handle energy surges as high as 50,000 volts, 1000 amps, rise times of 4 μsec, and total actuation times as long as 50 μsec without vaporizing as other lower capacity shunts do It is understood that while certain forms of the present invention have been illustrated and described herein, it is not to be limited to the specific forms or arrangements of parts described and shown.

We claim:

1. A device for protecting an EED from nearby lightning-induced inadvertent firing, or actuation comprising:
   A) an input lead for connecting an EIE to a DC power source to pass heating current through said EIE;
   B) a ground element electrically connected to said input lead by a first impedance; and
   C) a protective impedance in said input lead between said DC power source and said EIE which is greater than said first impedance when exposed to RF energy, said protective impedance being doped with calcium oxide.

2. The device defined in claim 1 wherein said doping is between 1 ppm and 20 ppm.

3. The device defined in claim 2 wherein said doping is about 10 ppm.

4. The device defined in claim 2 wherein said protective impedance includes a Ferrite element.

5. The device defined in claim 4 wherein said ferrite element is doped with calcium oxide in the range between 1 ppm and 20 ppm.

6. The device defined in claim 5 wherein said ferrite element includes MN-67 ferrite.

7. The device defined in claim 5 wherein said Ferrite element has an elemental formulation of $MnO_{0.45}ZnO_{0.3}FeO_{0.25}Fe_2O_4$.

8. The device defined in claim 5 wherein said Ferrite element is in the form of a bead device.

9. The device defined in claim 5 wherein said Ferrite element is in the form of a balun device.

10. The device defined in claim 5 wherein said Ferrite element is in the form of a choke device.

11. The device defined in claim 5 wherein said Ferrite element is in the form of an iron-rich, manganese-zinc ferrite formulation.

12. The device defined in claim 5 wherein said Ferrite element has a Curie temperature in excess of 250° C.

13. The device defined in claim 1 wherein said EIE has an internal DC resistance, said protective impedance has an internal DC resistance greater than said EIE internal DC resistance.

14. The device defined in claim 1 wherein said impedance has a DC resistance, said input lead has a DC resistance, and wherein said protective impedance has a dielectric coefficient which is sufficient to allow said protective impedance to function as a capacitor; said protective impedance having a DC resistance that is greater than the DC resistance of the EIE.

15. The device defined in claim 1 wherein said protective impedance is a lossy ferrite with a Curie Temperature in excess of 180° C.

16. The device defined in claim 15 wherein said lossy ferrite is doped with calcium oxide in a range between 1 ppm and 20 ppm.

17. The device defined in claim 15 wherein said lossy ferrite is an elemental formulation of $MnO_{0.45}ZnO_{0.3}FeO_2O_4$.

18. A device for protecting electronic components comprising:
   A) a metal casing having an open end;
   B) a closure element covering said case open end and including
      (a) an input lead for connecting an electronic element to a power source to pass current through said electronic element,
      (b) a ground element electrically connected to said input lead by a first impedance, and
      (c) a protective impedance in said input lead between said power source and said electronic element which is greater than said first impedance when exposed to RF energy, said protective impedance element including Ferrite material that has been doped with Calcium Oxide.

19. The device defined in claim 18 wherein said electronic element includes an EED EIE.

20. The device defined in claim 18 further including a filter unit connected to the electronic element.

21. The device defined in claim 18 wherein said metal case is said ground element, and said protective impedance is electrically connected to said metal case.

22. The device defined in claim 18 wherein said electronic element has an internal DC resistance, said protective impedance has an internal DC resistance greater than said electronic element internal DC resistance.

23. The device defined in claim 18 wherein said closure element is force fit into said metal case.

24. A device for protecting an electroexplosive device from lightning induced inadvertent actuation comprising:
   A) an impedance element having an impedance;
   B) an input lead which connects an ignition element to a source of DC power and which has an impedance that is greater than the impedance of the impedance element, said impedance element electrically connecting said input lead to a ground element, said input lead being electrically connected to said impedance element;
   C) an electrically conductive wall surrounding the ignition element, said impedance element being mounted on said conductive wall, and including Ferrite material that has been doped with Calcium Oxide.

25. A device for protecting electronic components comprising:
   A) an electrically conductive case having an open end and an internal DC resistance;
   B) an impedance element electrically connected to said electrically conductive case, said impedance element having an internal DC resistance and an impedance;
   C) an input lead connecting a source of DC power to an electronic element located inside said electrically conductive case, said input lead having an impedance and being electrically connected to said impedance element, said electronic element having an internal DC resistance, the internal DC resistance of said impedance element being greater than the internal DC resistance of said electronic element;
   D) said input lead being electrically separated from said electrically conductive case by a first impedance; and
   E) said first impedance being less than the impedance on said input lead, said impedance element including a Ferrite material that has been doped with Calcium Oxide.

26. The device defined in claim 25 wherein said input lead extends through said impedance element in a spiral pattern.

27. The device defined in claim 25 wherein said input lead is a paramagnetic material.

28. A method of protecting an electronic device comprising:
   A) encasing an electronic device in an open-ended electrically conductive case, the electronic device having an internal DC resistance;
   B) connecting the electronic device to a source of DC power using an input lead, there being a first impedance between the input lead and the conductive case;
   C) doping a ferrite element with calcium oxide to establish an internal DC resistance of the ferrite element that is greater than the internal resistance of the electronic device;
   D) electrically connecting the input lead to the ferrite element; and
   E) formulating the ferrite element to establish an impedance between the input lead and the case that is less than the impedance between the DC power source and the electronic device along the input lead for RF energy.

29. The method defined in claim 28 further including a step of force fitting the doped ferrite element into the conductive case.

* * * * *